(12) United States Patent
Shin et al.

(10) Patent No.: US 11,596,315 B1
(45) Date of Patent: Mar. 7, 2023

(54) MEASUREMENT OF VITAL SIGNS BASED ON IMAGES RECORDED BY AN EGOCENTRIC CAMERA

(71) Applicant: GOOGLE LLC, Mountain View, CA (US)

(72) Inventors: Dongeek Shin, Santa Clara, CA (US); Shwetak N. Patel, Seattle, WA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 17/448,285

(22) Filed: Sep. 21, 2021

(51) Int. Cl.
| | |
|---|---|
| H04N 7/18 | (2006.01) |
| A61B 5/0205 | (2006.01) |
| H04N 5/77 | (2006.01) |
| H04N 5/262 | (2006.01) |
| H04N 5/14 | (2006.01) |
| G06T 7/00 | (2017.01) |
| A61B 5/024 | (2006.01) |
| A61B 5/08 | (2006.01) |
| G06T 7/246 | (2017.01) |

(52) U.S. Cl.
CPC ........ *A61B 5/0205* (2013.01); *A61B 5/02438* (2013.01); *A61B 5/0816* (2013.01); *G06T 7/0016* (2013.01); *G06T 7/248* (2017.01); *H04N 5/144* (2013.01); *H04N 5/2628* (2013.01); *H04N 5/77* (2013.01); *G06T 2207/10016* (2013.01); *G06T 2207/30048* (2013.01)

(58) Field of Classification Search
CPC . A61B 5/0205; A61B 5/02438; A61B 5/0816; H04N 5/77; H04N 5/2628; H04N 5/144; G06T 7/0016; G06T 7/248; G06T 2207/30048; G06T 2207/10016
USPC ....... 348/158, 143, 151, 152, 153, 154, 155, 348/156; 386/210, 223, 224, 226
See application file for complete search history.

(56) References Cited

U.S. PATENT DOCUMENTS

| | | | |
|---|---|---|---|
| 9,339,210 B2 * | 5/2016 | Kersten | G16H 20/40 |
| 2015/0265161 A1 | 9/2015 | Hernandez et al. | |
| 2016/0210747 A1 * | 7/2016 | Hay | G01N 29/44 |
| 2020/0037946 A1 | 2/2020 | Mason et al. | |

OTHER PUBLICATIONS

Garde, et al., "Estimating Respiratory and Heart Rates from the Correntropy Spectral Density of the Photoplethysmogram", PLoS ONE 9(1): e86427. doi:10.1371/journal.pone.0086427, Jan. 22, 2014, 11 pages.

(Continued)

*Primary Examiner* — Robert Chevalier
(74) *Attorney, Agent, or Firm* — Brake Hughes Bellermann LLP

(57) ABSTRACT

A method for determining one or more vital signs of a person includes recording video images of a scene with an egocentric camera coupled to the person's body, detecting and magnifying image frame-to-image frame movements in the video images of the scene, representing the magnified image frame-to-image frame movements in the video images of the scene by a one-dimensional (1D) amplitude-versus-time series, and transforming the 1D amplitude-versus-time series representation into a frequency spectrum. The method further includes identifying one or more local frequency maxima in the frequency spectrum as corresponding to one or more vital signs of the person.

20 Claims, 11 Drawing Sheets

(56) References Cited

OTHER PUBLICATIONS

McDuff, et al., "Pulse and Vital Sign Measurement in Mixed Reality using a HoloLens", VRST '17, Nov. 8-10, 2017, Gothenburg, Sweden, 9 pages.

Ordóñez, et al., "Detection of human vital signs in hazardous environments by means of video magnification", PLoS ONE 13(4): e0195290. (https://doi.org/10.1371/journal.pone.0195290), Apr. 11, 2018, 9 pages.

International Search Report and Written Opinion for PCT Application No. PCT/US2022/076465, dated Jan. 17, 2023, 13 pages.

Liu, et al., "Detecting Pulse Rates From Facial Videos Recorded in Unstable Lighting Conditions: an Adaptive Spatiotemporal Homomorphic Filtering Algorithm", IEEE Transactions on Instrumentation and Measurement, vol. 70, 2021, 16 pages.

Wu, et al., "Eulerian Video Magnification for Revealing Subtle Changes in the World", ACM Transactions on Graphics vol. 31, No. 4, Article 65, Jul. 2012, pp. 65:1 to 65:8.

Zhang, et al., "Respiratory Rate Monitoring From the Photoplethysmogram Via Sparse Signal Reconstruction", IOP Publishing, Institute of Physics and Engineering in Medicine; Physiol. Meas. 37, 2016, pp. 1105-1119.

\* cited by examiner

Roughly ½ seconds

300

Recording video images of a scene with an egocentric camera coupled to a person's body
910

Detecting and magnifying image frame-to-image frame movements in the video images of the scene
920

Representing the magnified image frame-to-image frame movements in the video images of the scene by a one-dimensional (1D) amplitude-versus-time series
930

Transforming the amplitude-versus-time series representation into a frequency spectrum
940

Identifying one or more local frequency maxima in the frequency spectrum as corresponding to one or more vital signs of the person
950

MEASUREMENT OF VITAL SIGNS BASED ON IMAGES RECORDED BY AN EGOCENTRIC CAMERA

TECHNICAL FIELD

This description relates to measurement of vital signs of a person

BACKGROUND

Vital signs are measures of the body's most basic functions. The vital signs of a person can include, for example, blood pressure (BP), heart rate (HR), respiratory rate (RR), blood oxygen saturation, and core temperature, etc. Measurements of the vital signs are necessary to assess the clinical situation of a person. The vital signs of a person may be intrusively measured, for example, several times a day, by nurses in a clinical or hospital setting, or at home, or at the site of a medical emergency, etc. Early warning scores (EWS) based on the measured vital signs are generally calculated three times a day in clinical settings, but these may not capture early deterioration.

Wearable devices or sensors for measuring the vital signs provide an opportunity for remote monitoring of clinically relevant vital signs in non-clinical settings. The devices may allow patients to self-monitor, track, and assess human physiological data, while also providing interfaces (e.g., wireless interfaces) for communicating vital signs data to healthcare providers. Having a wearable device or sensor for measuring the vital signs decreases the restrictions placed on the patients' mobility and daily activities, and allows monitoring in the patients' natural environments (e.g., at home, at work, or during other activity). Such monitoring of the vital signs with wearable devices or sensors might detect clinical deterioration at an earlier stage and allow prompt corrective actions.

SUMMARY

In a general aspect, a method for determining one or more vital signs of a person includes recording video images of a scene with an egocentric camera coupled to the person's body, detecting and magnifying image frame-to-image frame movements in the video images of the scene, representing the magnified image frame-to-image frame movements in the video images of the scene by a one-dimensional (1D) amplitude-versus-time series, and transforming the 1D amplitude-versus-time series representation into a frequency spectrum. The method further includes identifying one or more local frequency maxima in the frequency spectrum as corresponding to one or more vital signs of the person.

In a general aspect, a computer program product is tangibly embodied on a non-transitory computer-readable storage medium. The storage medium includes instructions that, when executed by at least one computing device coupled to an egocentric camera disposed on a person, are configured to cause the at least one computing device to: record video images of a scene using the egocentric camera; detect and magnify image frame-to-image frame movements in the video images of the scene; represent the magnified image frame-to-image frame movements in the video images of the scene by a one-dimensional (1D) amplitude-versus-time series; transform the 1D amplitude-versus-time series representation into a frequency spectrum; and identify one or more local frequency maxima in the frequency spectrum as corresponding to one or more vital signs of the person.

In a general aspect, a computing device includes a processor and a storage medium storing instructions. The instructions, when executed by the processor, cause the computing device to: record video images of a scene using the egocentric camera; detect and magnify image frame-to-image frame movements in the video images of the scene; represent the magnified image frame-to-image frame movements in the video images of the scene by a one-dimensional (1D) amplitude-versus-time series; transform the 1D amplitude-versus-time series representation into a frequency spectrum; and identify one or more local frequency maxima in the frequency spectrum as corresponding to one or more vital signs of the person.

The details of one or more implementations are set forth in the accompanying drawings and the description below. Other features will be apparent from the description and drawings, and from the claims.

BRIEF DESCRIPTION OF THE DRAWINGS

FIG. 9 is a flowchart illustrating an example method for measuring the vital signs of a person.

DETAILED DESCRIPTION

Figure 1:
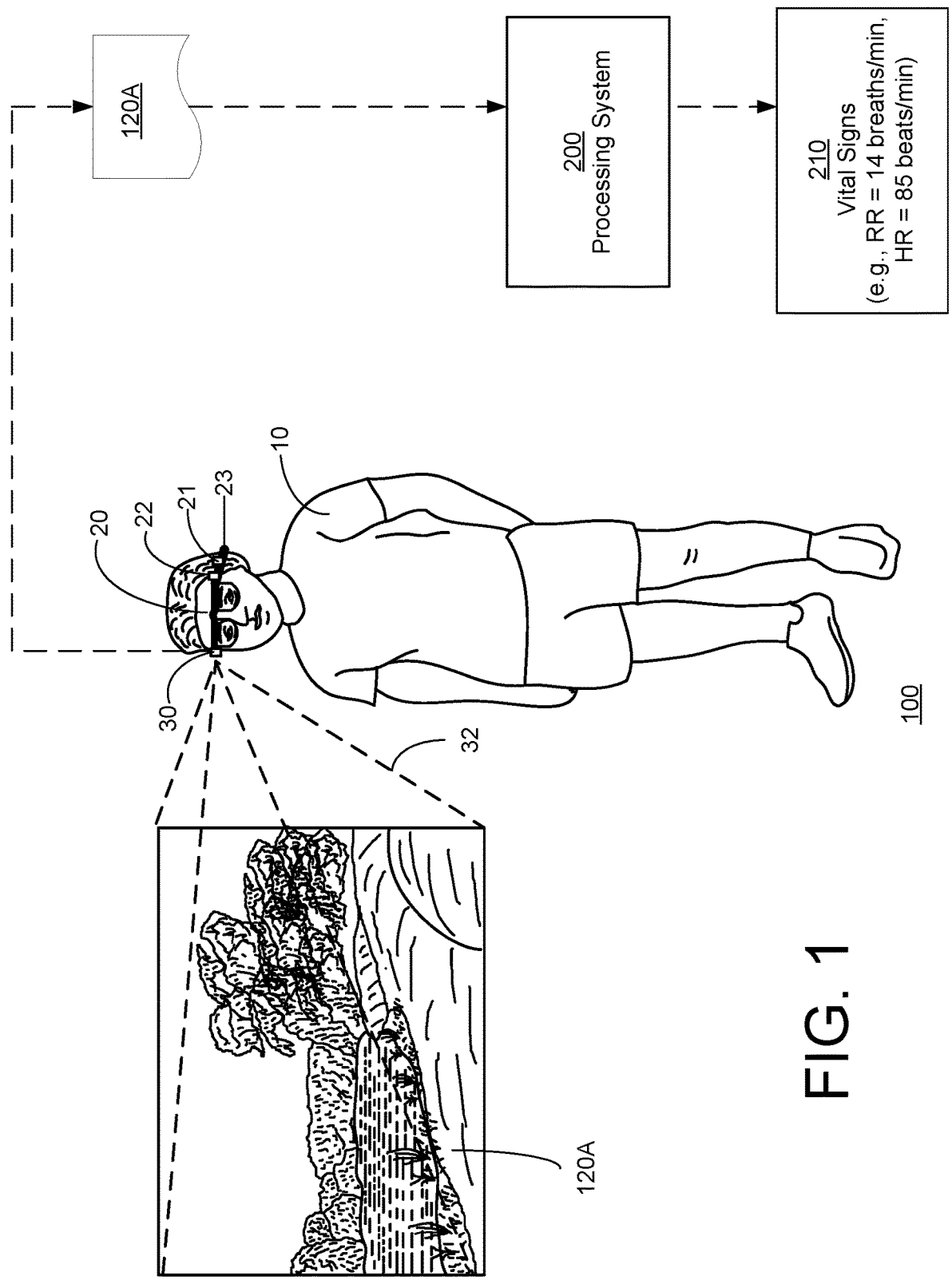
FIG. 1 is a schematic illustration of a scenario in which a person's vital signs can be measured via a wearable device (e.g., glasses).

Systems and methods (collectively "solutions") for measuring a person's vital signs (e.g., heart rate, heart rate variability, respiration rate, etc.) are described herein. The solutions involve a wearable device worn by, or otherwise physically coupled to the body of, the person. The wearable device includes an egocentric camera (e.g., a forward facing camera) configured to capture images and videos of scenes in the surroundings of the person (i.e., in the field-of-view (FoV) of the egocentric camera). The solutions involve motion analysis of the images and videos of scenes captured by the egocentric camera to determine the vital signs (such heart rate, heart rate variability, respiration rate, etc.) of the person.

The person's body may exhibit natural respiratory and cardiac body movements (albeit weak movements) caused by, or related to, the person's respiration cycles (i.e., breathing in and out) and the person's cardiac cycles (i.e., heartbeats including alternating periods of the heart muscle relaxing and refilling with blood, and robust contraction and pumping of blood). A normal respiration rate for an adult person at rest can be, for example, in a range of about 10 to about 25 breaths per minute (or equivalently at a (wave) frequency in a range of about 0.17 Hz to 0.33 Hz, where frequency is the inverse of rate). A normal resting heart rate for an adult person can be, for example, in a range of about 60 beats per minute to about 100 beats per minute (or equivalently at a (wave) frequency in a range of about 1.0 Hz to 1.67 Hz).

The position (and FoV) of the egocentric camera coupled to the person's body, at any given time, may be responsive to the person's respiratory and cardiac body movements (in other words, the position of the egocentric camera may change and move along with the person's respiratory and cardiac body movements). The changing positions of the egocentric camera (in other words, camera shake) may cause movement (e.g., vibration or jitter) in the images and videos of the scenes captured by the egocentric camera.

Motion analysis (including frequency analysis) of the images and videos of scenes captured by the egocentric camera can be used to determine the vital signs (e.g., a respiration rate (RR), a heart rate (HR), etc.), in accordance with the principles of the present disclosure.

In example implementations, the wearable device may include, or be coupled to, one or more computers (e.g., a computing device). The computing device may be connected to the egocentric camera by wires or wirelessly. The computing device may be configured to operate the egocentric camera, and to collect and analyze the images and videos of scenes captured by the egocentric camera to determine the vital signs of the person.

In example implementations, the person may have only a passive role or an inactive role in the vital signs measurements. The wearable device and the computing device may be configured to determine the person's vital signs without requiring active participation of the person. The person can go about doing his or her activities (e.g., routine activities such as sitting on a couch in a living room, sitting on chair at desk, reading a book, watching a show, or watching a natural scene or any real world scene in an or indoor outdoor environment, etc.) even as his or her vital signs are being measured via the wearable device.

In example implementations, the egocentric camera may be an ordinary or commodity camera (i.e., a camera constructed using off-the shelf image sensors and other components) or one that is not particularly customized for vital signs measurements.

In example implementations, the wearable device may be a pair of optical glasses (e.g., Augmented Reality (AR) glasses) worn by the person. The egocentric camera and the computing device may be included in, or attached to, the glasses worn by the person.

In example implementations, the egocentric camera may be a pre-existing camera (e.g., a forward facing camera) that is often available or included in common AR glasses designs. Notably, the egocentric camera may not see the face of the person wearing the AR glasses. Instead, the egocentric view camera (included in the AR glasses) sees scenes of the surrounding environment in which the person is situated.

FIG. 1 is a schematic illustration of a scenario 100 in which a person's vital signs can be measured via a wearable device (e.g., glasses 20), in accordance with the principles of the present disclosure.

In scenario 100, the person (e.g., person 10) may be seated in an outdoor environment partaking, for example, his or her natural surroundings. Person 10 may be wearing a wearable device including an egocentric camera 30 physically attached or coupled to the person's body. The wearable device may (including egocentric camera 30) may be an article of clothing (e.g., a shirt, a coat, a hat), an accoutrement or article of jewelry (e.g., a brooch, a necklace, a bracelet, a neck lanyard, a neck wallet, a waist band, a pocket pen holder, etc.). In an example implementation, the wearable device (e.g., as shown in FIG. 1) may be a pair of glasses (e.g., glasses 20) worn by the person. Egocentric camera 30 may be physically attached or coupled to the person's body via (a frame of) glasses 20.

In example implementations, the wearable device may include a device on/device off sensor (e.g., a capacitive sensor) indicating when the wearable device is actually worn by the person. For example, the wearable device (e.g., glasses 20) may include a capacitive Don/Doff sensor 21 disposed on a temple piece 23 of the glasses and which senses (e.g., capacitively) when the wearable device (e.g., glasses 10) is actually worn by the person. Sensor 21 may be configured to activate egocentric camera 30 to capture images only when the wearable device is actually worn by the person.

In example implementations, the wearable device may include one or more motion sensors (e.g., an inertial motion unit (IMU) sensor) capable of detecting if person 10 is in a stationary posture (e.g., is not moving or is in a sedentary position) or in a non-stationary posture (e.g., moving, walking, or running around) when the wearable device is actually worn by the person. For example, the wearable device (e.g., glasses 20) may include, for example, an IMU sensor 22 disposed on temple piece 23 of the glasses. Sensor 22 may be configured to activate egocentric camera 30 only when person 10 is in a stationary posture.

Egocentric camera 30 as worn by the person could be facing any direction (e.g., toward the front, side, or back of the person). Egocentric camera 30 may be configured to take (i.e., record) images (e.g., image frame 120A) of a scene in a field-of-view (e.g., FoV 32) of the camera. and transmit the images (e.g., image frame 120A) to an image processing system for vital signs analysis. In example implementations, egocentric camera 30 may be coupled (by wire or wirelessly) to the image processing system (e.g., image processing system 200, FIG. 2).

Figure 2:
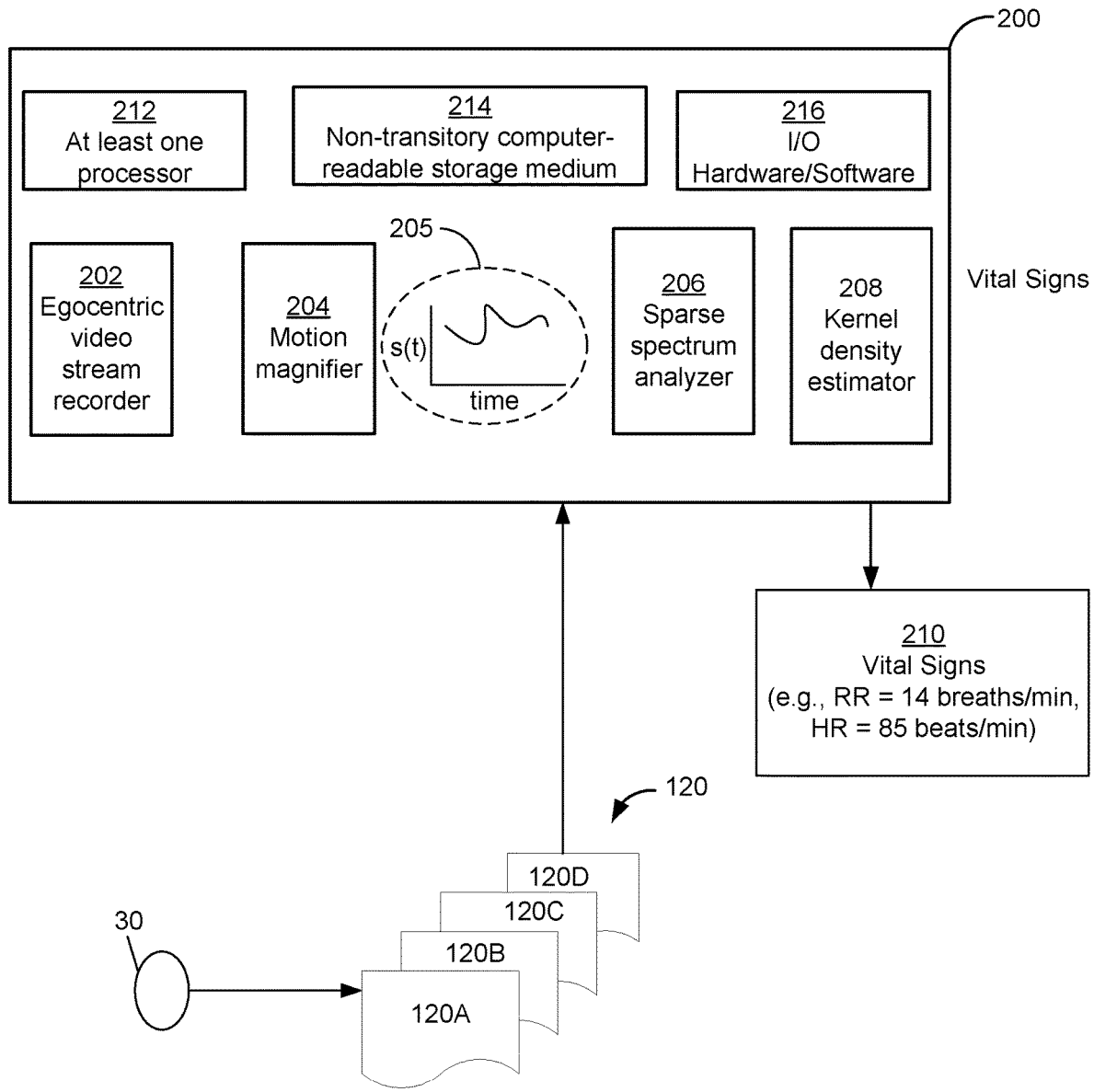
FIG. 2 is a block diagram illustrating an example image processing system.

As shown in FIG. 2, image processing system 200 may include at least one processor (e.g., processor 212), a non-transitory computer-readable storage medium (e.g., medium 214), and input/output (I/O) hardware and software (e.g., I/O 216). In an example implementation, system 200 may be disposed on one or more remote computing devices (not shown). In some example implementations, a portion of system 200 (e.g., a processor) may be disposed in the wearable device (e.g., glasses 20) in proximity to egocentric camera 30. Other portions of system 200 may be disposed on one or more remote computing devices (e.g., wirelessly connected computing devices). In some example implementations, all of system 200 may be disposed on one or more remote computing devices.

Image processing system 200 may further include hardware and or software modules for an egocentric video stream recorder 202, a motion magnifier 204, a sparse frequency spectrum analyzer 206, and a kernel density estimator 208. The modules may include algorithms to process images captured by egocentric camera 30 attached to a wearable device (e.g., glasses 10) to estimate vital signs 210 (e.g., RR=14 breaths/min, HR=85 beats/min) of the person wearing the wearable device.

Egocentric video stream recorder 202 may be configured to receive or retrieve a stream of images (e.g., video stream 120) from camera 30. Video stream 120 may include a time series of image frames (e.g., images 120A, 120B, 120C, and 120D, etc.) captured by egocentric camera 30 (e.g., in scenario 100). Egocentric video stream recorder 202 may record or persist the image frames captured over a time interval in a memory (e.g., medium 214) for further frequency analysis and vital signs extraction.

Motion magnifier 204 may include algorithms (code) to identify changes (or movements) between the image frames captured over the time interval, and further magnify (or amplify) the identified image frame-to-image frame changes or movements in the images. The image frame-to-image frame changes may be subtle changes that are invisible or are only weakly visible to the naked human eye. The image frame-to-image frame changes may include image movements caused by camera movement (e.g., due to camera shake). The camera movements may be responsive, for example, to the person's respiratory and cardiac body movements. Motion magnifier 204 may extract a one-dimensional time series representation of the amplitudes s(t) of the image frame-to-image frame movements (in other words, extract an amplitude-versus-time representation) (e.g., s(t) motion curve 205) for further analysis. Motion curve 205 may represent the amplified amplitude of motion of the detected image frame-to-image frame changes. Motion curve 205 may be noisy with movements of camera 30 due to causes other than the person's respiratory and cardiac body movements (e.g., other causes such as walking, or running, jogging or otherwise being non-stationary) superimposed on movements due to the person's respiratory and cardiac body movements.

Image processing system 200 may further include a sparse frequency spectrum analyzer 206 and a kernel density estimator 208 for frequency analysis of the magnified image frame-to-image frame changes represented by the one-dimensional time series representation (e.g., motion curve 205) toward determining the vital signs of the person.

Sparse frequency spectrum analyzer 206 may perform a frequency analysis of magnified amplitude-vs-time motion curve 205 and transform (e.g., Fourier transform) the motion curve in to a frequency spectrum (i.e., an amplitude-vs-frequency curve). Sparse frequency spectrum analyzer 206 may further convolve the frequency spectrum with a kernel (e.g., a gaussian filter) to further smooth out the frequency spectrum and pick out local maxima that correspond to the person's respiratory and cardiac body movements for the vital signs determinations (i.e., HR and RR determinations). The frequency spectrum may include frequency ranges or bands extending over the frequencies of the person's respiratory and cardiac body movements. The frequency spectrum may, for example, extend from about 0 Hz to 2.0 Hz (including the frequency band of about 0.17 Hz to 0.33 Hz covering the person's respiratory activity and or the frequency band of about 1.0 Hz to 1.67 Hz covering the person's heart activity).

Kernel density estimator 208 may convolve the frequency spectrum with a kernel (e.g., a gaussian filter) to further smooth out the frequency spectrum and pick out local maxima that correspond to the person's respiratory and cardiac body movements for the vital signs determinations (i.e., RR and HR determinations).

Figure 3:
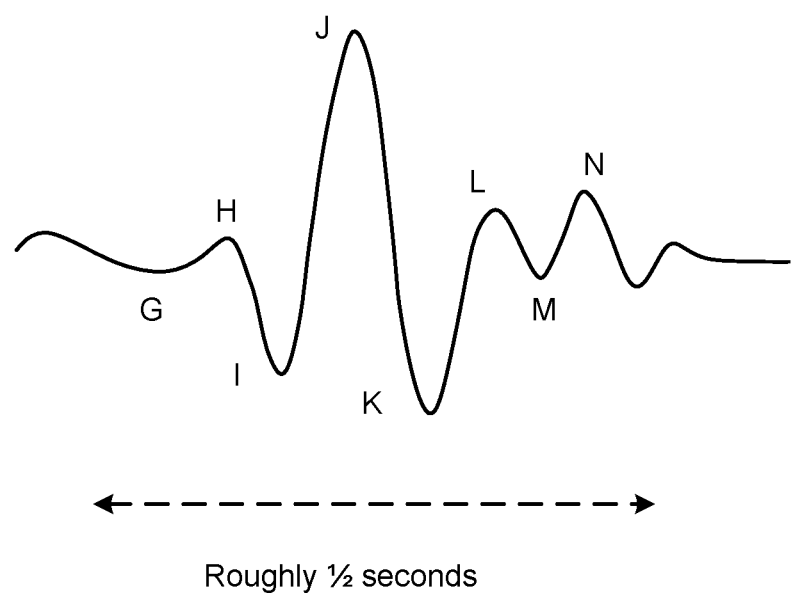
FIG. 3 is a graph of a ballistocardiogram (BCG).

In example video stream 120 (received by egocentric video stream recorder 202) may include image frames captured by camera 30 at a specific image sampling rate in consideration of the range of frequencies involved in a person's heart rate, respiratory rate, and body movement. It is known that the person's body moves with each heartbeat. These movements (albeit subtle movements) represent the body's mechanical recoil to cardiac expulsion of blood into the arteries and or chest movements due to breathing. A ballistocardiogram (BCG) represents the ballistic forces of the heart generated by a person's heart rate, respiration rate, and body movement. FIG. 3 shows an example of a typical ballistocardiogram (BCG) 300 for one heartbeat of a healthy person. In the example shown, the BCG includes several wave peaks which are marked by letters (e.g., G, H, I, J, K, L, M, and N). A peak-to-peak time interval for the waves in BCG 300 (e.g., between the H and I peaks or the I and J peaks) is approximately 0.5 seconds*(1/7)=0.0714 seconds. Thus, a frequency content of waves in BCG 300 is below an upper frequency limit=1/0.0714 seconds=14 Hz. Based on frequency content of waves in BCG 300 being below the upper frequency limit=14 Hz and Nyquist's information sampling theorem, a "Nyquist" image sampling rate of about 2×14 Hz=28 Hz should be sufficient to capture all information related to the person's heart and respiration activity in video stream 120. In example implementations, the egocentric camera (e.g., camera 30) may be configured to capture image frames for video stream 120 at a camera resolution at about, or greater than the Nyquist image sampling rate=28 Hz (e.g., at 25 Hz, 28 Hz, or 30 Hz) (in other words, at a frame rate greater than about 1500 frames/minute).

A VGA (640×480) display resolution corresponds to a refresh frequency or rate of about 60 Hz (i.e., a rate greater than 28 Hz). In example implementations, the egocentric camera (e.g., camera 30) may be configured to capture image frames for video stream 120 at a camera resolution equal to, or greater than, the VGA (640×480) resolution refresh frequency (~60 Hz).

Figure 4:
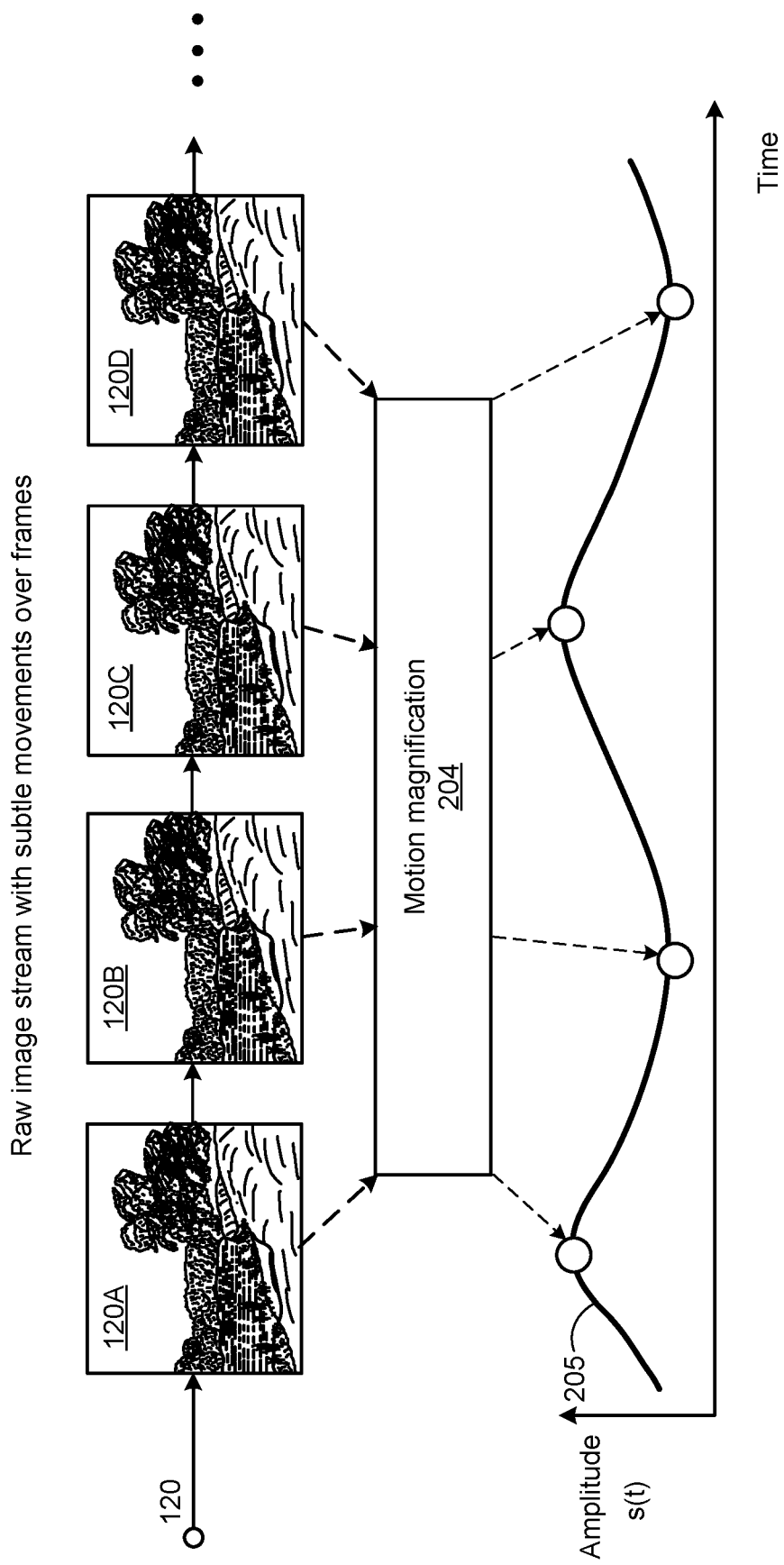
FIG. 4 pictorially illustrates example image frames that may be captured by an egocentric camera in the scenario of FIG. 1.

FIG. 4 pictorially shows image frames (e.g., image frames 120A, 120B, 120C, and 102D, etc.) that may be captured by camera 30 in scenario 100 (FIG. 1) at a sampling rate greater than about 28 Hz and streamed (in video stream 120) to system 200 for analysis by motion magnifier 204. Motion magnifier 204 may detect subtle scene changes in the sequence of image frames (e.g., image frames 120A, 120B, 120C, and 102D, etc.). Motion magnifier 204 may represent the image frame-to-image frame subtle changes as a one-dimensional amplitude time series as an amplitude versus time curve (e.g., motion curve 205). Motion curve 205 may have a same frequency content of a BCG waveform (e.g., BCG 300) of the person and include frequency content relating to the person's vital signs (e.g., HR and RR).

In example implementation, as shown in FIG. 4, motion magnifier 204 may use phase-based motion magnification algorithms to magnify image frame-to-image frame changes pixel by pixel to generate a magnified-movements video. Motion magnifier 204 may track and magnify subtle inter-frame changes in video stream 120. Motion magnifier 204 may further generate the one-dimensional time series representation of the magnified changes (e.g., s(t) motion curve 205) in video stream 120.

The algorithms in motion magnifier 204 may be based, for example, on an Eulerian Video Magnification (EVM) framework or technique, and may involve phase based pixel-by-pixel processing of the image frames. The EVM technique takes a video sequence (e.g., video stream 120) as input, applies spatial decomposition, followed by temporal filtering to the frames in the video stream. The technique shows or reveals phenomena occurring at temporal frequencies corresponding the vital signs of interest (i.e. HR, RR, etc.). The resulting signal is then amplified to reveal information hidden in the image frames.

Figure 5:
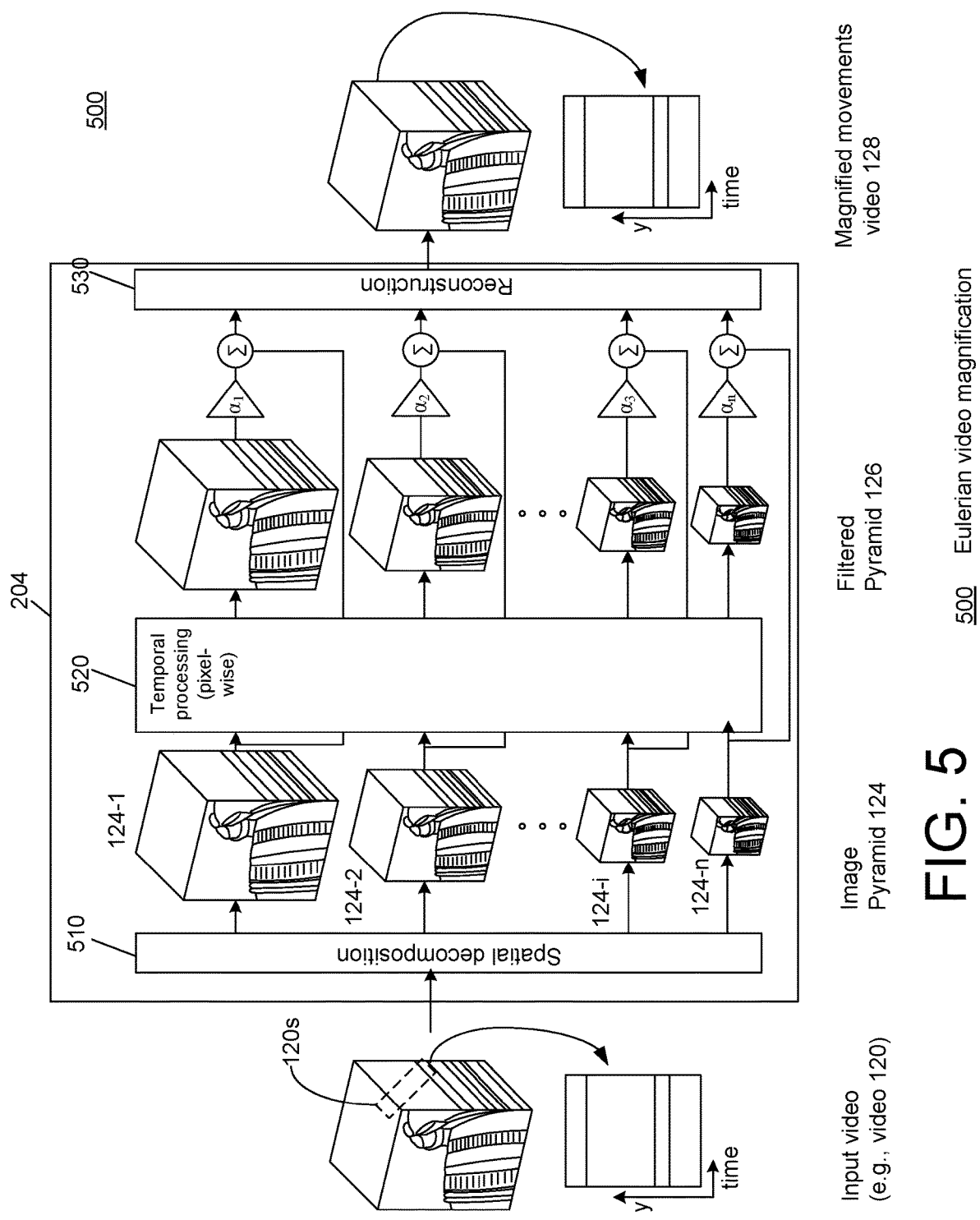
FIG. 5 is a block diagram illustrating an example motion magnifier.

As shown in FIG. 5, motion magnifier 204 may include a spatial decomposition layer 510, a temporal processing layer 520, and a reconstruction layer 530.

Spatial decomposition layer 510 may include algorithms to spatially decompose the input images into smaller image portions and to construct an image pyramid representation (e.g., a Lagrangian or gradient image pyramid 124) of the input images. In example implementations, image pyramid 124 may be a complex steerable pyramid with n layers (e.g., layer 124-1, layer 124-2, . . . , layer 124-I, and layer 124-n).

Each layer of the image pyramid 124 may be further processed through temporal processing layer 520. Temporal processing layer 520 may include algorithms to filter layers of the image pyramid and amplify only limited frequency ranges or bands to generate a filtered pyramid 126. The limited frequency ranges or bands amplified may include or extend over the frequencies of the person's respiratory and cardiac body movements (that correspond to the vital signs of interest such as HR, RR, etc.).

Further, reconstruction layer 530 in motion magnifier 204 may include algorithms to weigh and sum the layers of the filtered image pyramid 126 with the original pyramid (i.e., image pyramid 124) to reconstruct an output video (e.g., magnified movements video 128). Magnified movements video 128 may include (large) motion magnifications for the frequencies of interest. Motion magnifier 204 may further generate an amplitude signal s[t] motion curve 205 (FIG. 4) based on magnified movements video 128.

In some instances, extraneous movements unrelated directly to cardiac or respiratory activity (e.g., person 10 shaking or nodding his or her head, or walking or jogging, or other objects moving in the scene) may be superposed on, and obscure, the person's heart and respiratory related body movements recorded in the images. To avoid complications in the frequency analysis of the person's body movements to determine the heart rate or respiratory rate, motion magnifier 204 may process only portions or regions of the images that are at least relatively static and not disturbed by the extraneous movements. For example, to avoid imaging and analyzing vibrations resulting, for example, from the person's head jitter, shaking or nodding, or other moving objects in the scene (e.g., people walking across the scene, trees swaying, etc.), motion magnifier 204 include algorithms to run a multiclass object detector on the images to identify one or more unmoving or relatively static regions (e.g., relatively static region 120S in video 120, FIG. 5) and ignore the pixels that do not match the identified static regions of interest. For the pixels that describe the relatively static regions (such as walls and floors) in the scene, motion magnifier 204 may take an average of all the pixels (e.g., for reference value) and store the average over time. There can be many relatively static regions in one image.

An example snippet of code that may be included in motion magnifier 204 for averaging all the pixels in a static region may be as follows:

s[t]=mean({motion_mag_pixel_region_1[t], motion_magpixel_region_2[t], . . . , motion_mag_pixel_region_N[t]}), where motion_mag_pixel_region_i[t] describes a small i-th region of the motion magnified image that passes a test of being an object that is static.

Figure 6A:
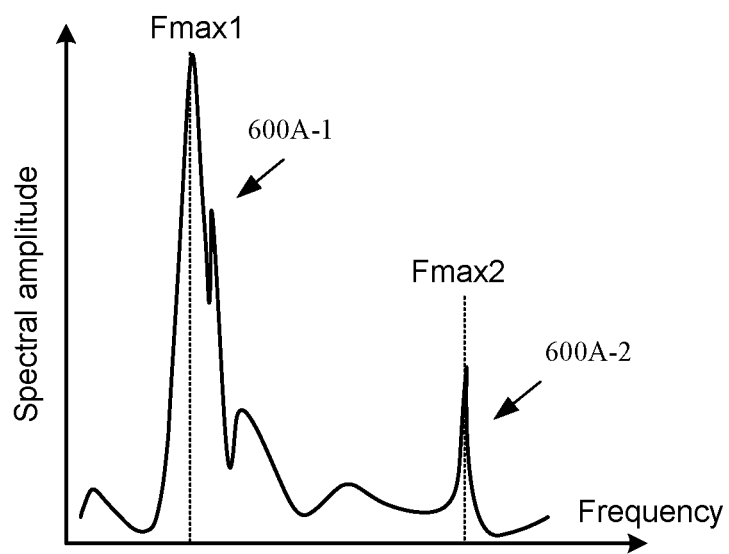
FIG. 6A is a graph illustrating an example sparse frequency spectrum.
Figure 6B:
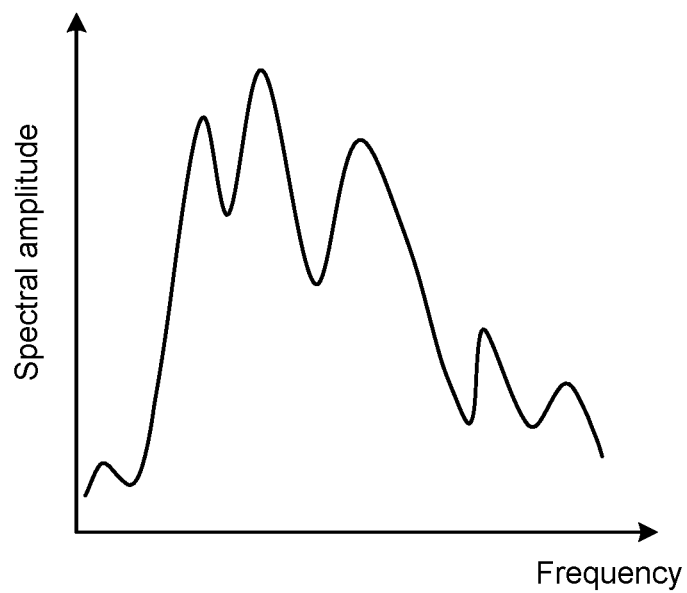
FIG. 6B is a graph illustrating an example non-sparse frequency spectrum.

In some instances when the movements recorded in the images are primarily those induced by the person's heart and respiratory activity, an amplitude signal s[t] (i.e., motion curve 205, FIG. 4) based on magnified movements video 128) may, in favorable circumstances, appear to be a sum of only two pseudo-sinusoids: one larger, lower-frequency sinusoid describing the periodic motion of breathing, another smaller, higher-frequency sinusoid describing the periodic movement caused by heartbeats, and may have a sparse frequency spectrum representing the sum of the person's heart and respiration related body movements. The sparse frequency spectrum (e.g., frequency spectrum 600A shown, for example, in FIG. 6A) may appear as a superposition of two pseudo-sinusoids: one larger, lower-frequency sinusoid 600A-1 describing the periodic motion of breathing; and another smaller, higher-frequency sinusoid 600A-2 describing the periodic movement caused by human heart beats. A frequency (Fmax1) corresponding to a maximum of the lower-frequency sinusoid 600A-1 may be attributed to the respiratory rate (rate $\propto$1/Fmax1) of the person, and a frequency (Fmax2) corresponding to a maximum of the higher-frequency sinusoid 600A-2 may be attributed to the heart rate (rate $\propto$1/Fmax2) of the person, In general instances, when other movements of the person (e.g., person 10, FIG. 1) or of other objects in the scene are captured in the images, an amplitude signal s[t] (i.e., motion curve 205, FIG. 4, based on magnified movements video 128) may have a non-sparse frequency spectrum. FIG. 6B shows an example of a non-sparse frequency spectrum 600B. The non-sparse frequency spectrum (e.g., frequency spectrum 600B shown, for example, in FIG. 6B) may appear as a noisy or cluttered superposition of many over lapping frequency pseudo-sinusoids describing the other movements in addition to the two pseudo-sinusoids describing the periodic motion of breathing and the periodic movement caused by human heart beats. Determination of the heart rate and respiratory rate from non-sparse frequency spectrums may not be reliable due to the noise from the over lapping pseudo-sinusoids describing the other movements.

In example implementations, for determination of the person's vital signs (e.g., HR and RR), non-sparse frequency spectrums (e.g., non-sparse frequency spectrum 600B, FIG. 6B) may be discarded. Only sparse frequency spectrums (e.g., sparse frequency spectrum 600A, FIG. 6A) may be used for determination of the person's vital signs (e.g., HR and RR), In example implementations, sparse frequency spectrum analyzer 206 may mathematically determine a sparsity measure of a frequency spectrum (e.g., frequency spectrum 600A or 600B), for example, as a ratio of a L2 Norm and a L1 Norm of the frequency spectrum as given by the expression:

sparsity (frequency spectrum)=L2 Norm (frequency spectrum)/L1 Norm (frequency spectrum).

The sparsity measure may have a higher value for a sparse frequency spectrum and a lower value for non-sparse frequency spectrum. For example, for a sparse frequency spectrum represented by an example vector [0, 0, 1, 0, 0, 1, 0, 0, 0, 0, 0], sparsity (frequency spectrum)=0.707, and for a dense or non-sparse frequency spectrum represented by an example vector [1, 2, 3, 4, 5, 6, 7, 8, 9, 10, 11], sparsity (frequency spectrum)=0.341.

In example implementations, a frequency spectrum may be selected or excluded from further processing to determine the person's vital signs based on the sparsity value of the frequency spectrum. In example implementations, a threshold sparsity value may be set, for example, at about 0.5. After a sparsity threshold check, only frequency spectrums with sparsity values greater than the threshold sparsity value (sparsity >0.5) may be further used for determining the vital signs (e.g., HH and RR) of the person.

Any spectral feature (e.g. a non-sparse frequency spectrum with a uniform or a more uniform-like frequency content) that violates this threshold condition may indicate that person was not a suitable stationary condition (during image capture by the egocentric camera) for reliable vital signs measurement. For example, the person may have been nodding or walking around introducing large extraneous image movements over and above the subtle heart and respiratory body movements captured by the egocentric camera. The sparsity threshold check may ensure that the vital signs determination is reliably based on a frequency spectrum that predominantly represents the person's respiratory and cardiac movements over other movements.

In some example implementations, in addition to, or as an alternate to, the sparsity threshold check, other techniques may be used to select or exclude a frequency spectrum for further processing to determine the person's vital signs. In an example implementation, these other techniques may involve using sensors (e.g., an inertial mass unit (IMU)) to determine whether the person was in a stationary posture (e.g., sedentary) or a non-stationary posture (i.e., moving) during image capture by the egocentric camera. Only images (and spectra) captured while the person was in a stationary posture may be processed to determine the person's vital signs. Images (and spectra) if captured while the person was in a non-stationary posture may be excluded from processing to determine the person's vital signs.

After a sparse frequency spectrum is selected for further processing, kernel density estimator 208 (in system 200, FIG. 2) may convolve the sparse frequency spectrum with a kernel (e.g., a gaussian kernel or filter) to further smooth out the frequency spectrum and pick out local maxima that correspond to the person's respiratory and cardiac body movements for the vital signs determinations (i.e., HR and RR determinations). In example implementations, the convolution operation of kernel density estimator 208 may be a simple convolution represented, for example, by the pseudo code: spectrum_output=conv(gaussian_kernel, spectrum_input).

Figure 7:
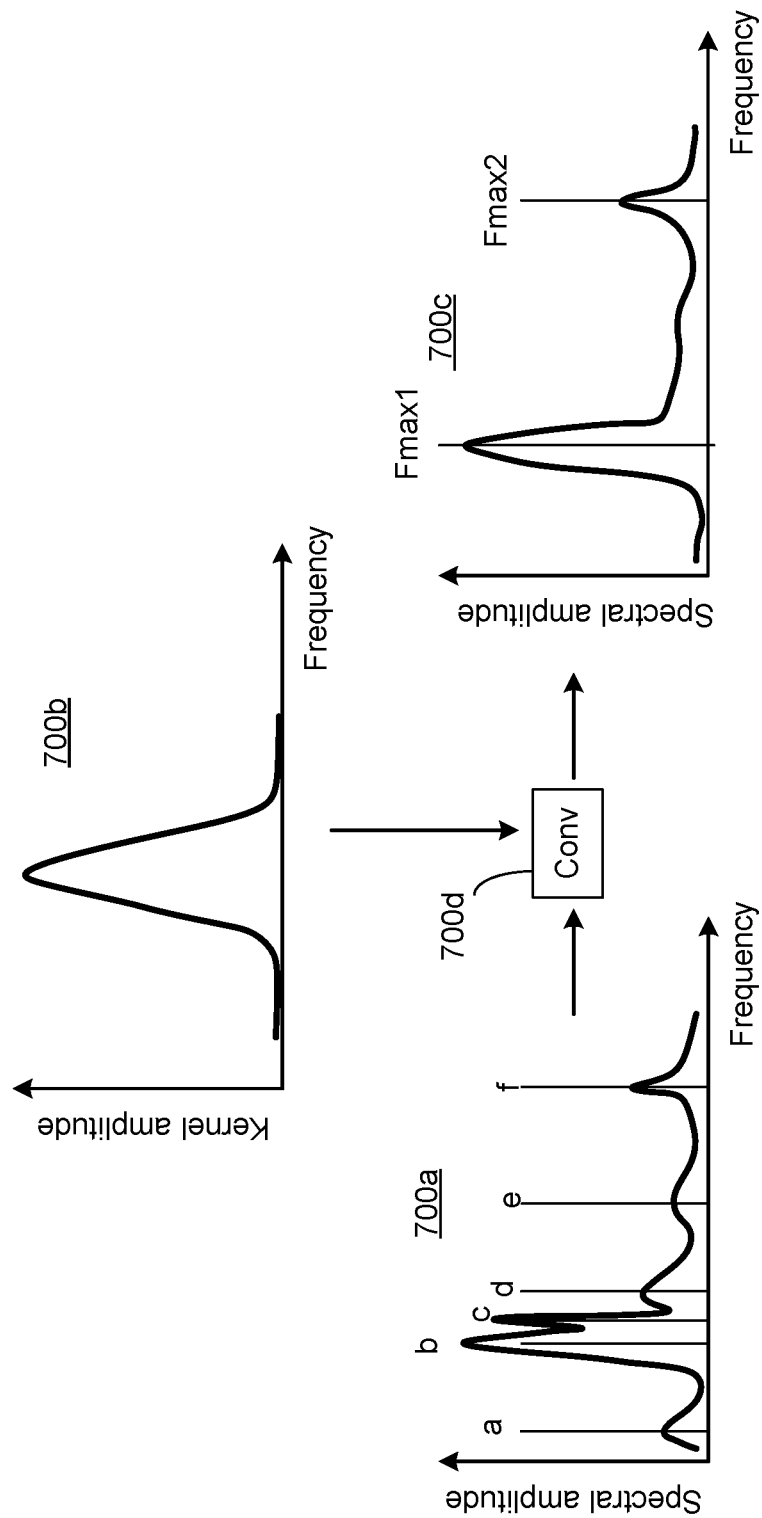
FIG. 7 is a schematic illustration of an example convolution of a kernel with a sparse frequency spectrum to obtain a smoothed frequency spectrum.

FIG. 7 schematically illustrates the convolution operation of kernel density estimator 208, for example, on a sparse frequency spectrum 700a, to obtain a smoothed frequency spectrum 700c.

As shown in FIG. 7, sparse frequency spectrum 700a may include a superposition of pseudo-sinusoids describing the periodic motion of breathing and describing the periodic movement caused by human heart beats. As discussed above with reference to FIG. 6A, some local frequency maxima (e.g., Fmax1 and Fmax 2, FIG. 6A) may be identified as corresponding to the respiratory rate and the heart rate of the person, However, sparse frequency spectrum 700a may be noisy or non-smooth with the pseudo-sinusoids including several peaks with local maxima at different frequencies (e.g., frequencies a, b, c, d, e, and f). The peaks with local maxima (e.g., at frequencies b and c) in the noisy spectrum may, for example, overlap. This overlap may introduce statistical uncertainty in identifying which one of the frequencies (e.g., frequency a or frequency b) is a correct measure of a vital sign (e.g., respiratory rate) of the person. The convolution of sparse frequency spectrum 700a by kernel density estimator 208 to generate smoothed frequency spectrum 700c may help reduce this statistical uncertainty in identifying the local maxima that are correct measures of the vital signs. Smoothed frequency spectrum 700c may, for example, have only two non-overlapping peaks with individual frequency maxima (e.g., at Fmax1 and Fmax2) that can be more definitely identified as measures of the person's vital signs (e.g., heart rate and respiratory rate) with more statistical certainty than from sparse frequency spectrum 700a.

Figure 8B:
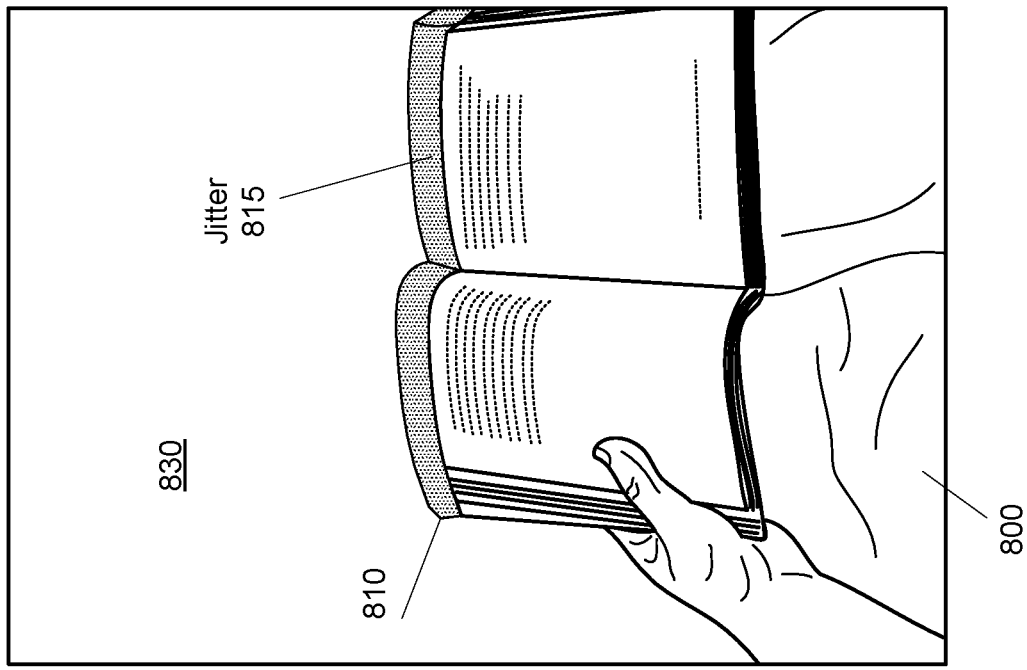
FIGS. 8A, 8B, and 8C are schematic illustrations of some example aspects of motion magnification by a system to determine a person's vital signs in an example test scenario.
Figure 8A:
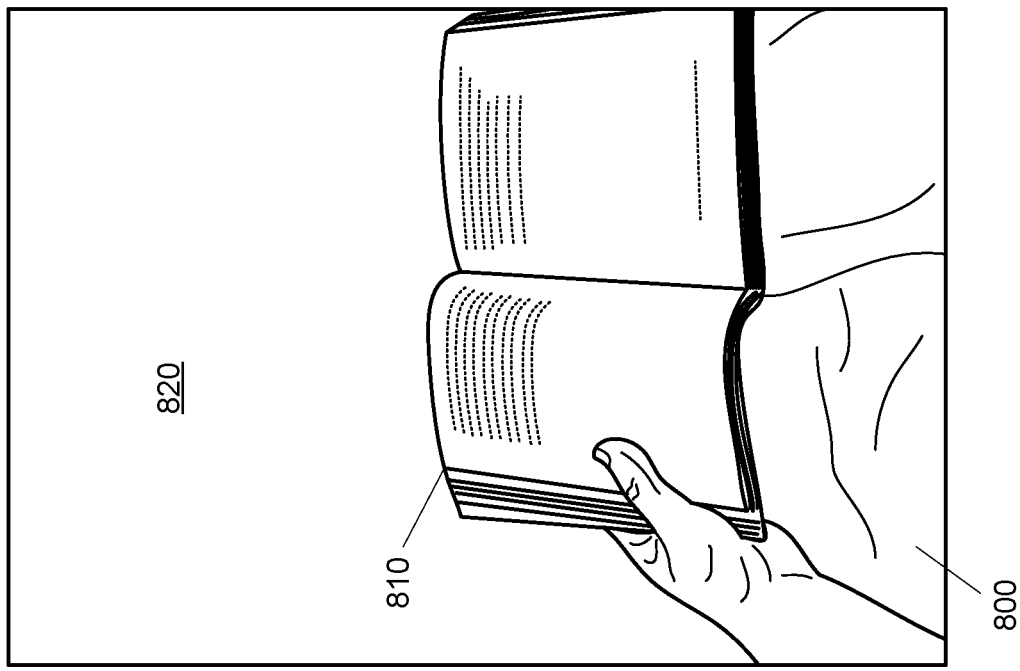
Figure 8C:
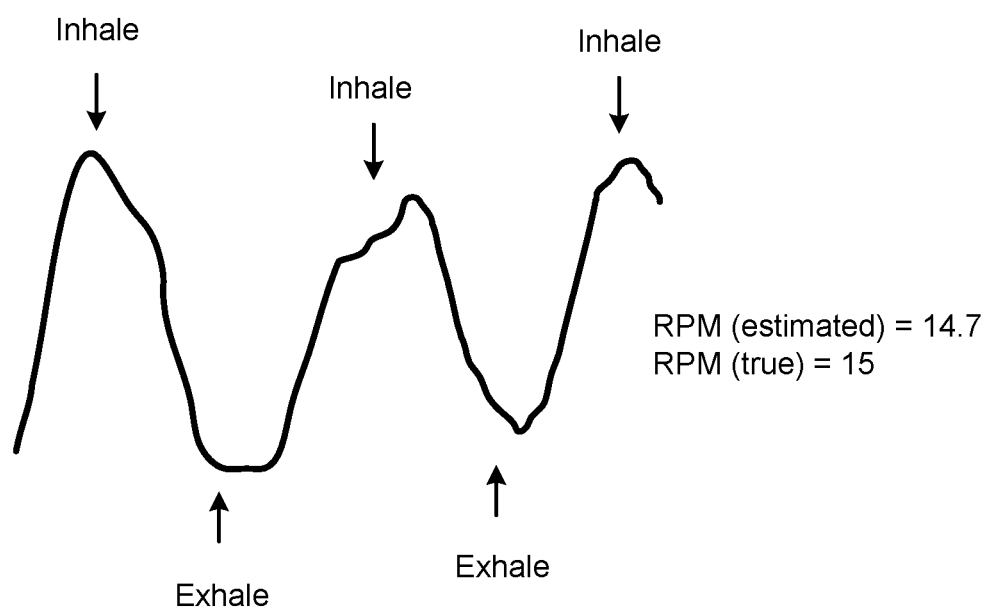

FIGS. 8A, 8B, and 8C schematically illustrate, for example, some aspects of motion magnification by system 200 to determine a person's vital signs in an example test scenario. In the test scenario, a person 800 (wearing wearable device 100, FIG. 1) may be seated passively (on a couch or chair (not shown)) and reading a book 810 placed on her lap. As shown in FIG. 8A, image frame 820 may represent an image that is captured by an egocentric camera (e.g., camera 30, FIG. 1) and is included in a video stream (e.g., video stream 120, FIG. 1) received by egocentric video stream recorder 202 in system 200 for vital signs determination.

Images (e.g., image frame 820) in video stream 120 may show no perceptible movements due to the person's heart or respiratory activity. However, motion magnifier 204 may (e.g., using the phase-based motion magnification techniques (e.g., EVM) described above) may generate a magnified movements video stream (e.g., like magnified movements video 128, FIG. 5) in which the subtle image movements (due person 800's respiratory activity) in video stream 120 are magnified.

FIG. 8B shows an image frame 830 as an example pictorial representation of magnified image frames in the magnified movements video 128. In image frame 830, the magnified motion obtained by motion magnifier 204 is shown, for purposes of illustration, as a region of jitter 815 at an edge of book 810. FIG. 8C illustrates a portion of a 1-D time series amplitude-vs-time motion curve 805 (similar to motion curve 205, FIG. 2, FIG. 4) representing the magnified image frame-to-image frame movements in the magnified movements video 128. Motion curve 805 extends over several inhalation-exhalation cycles of person's respiratory activity as indicated by the labels exhale and inhale in the figure.

In the test scenario, frequency analysis of motion curve 805 yielded a respiratory rate (RR) of 14.7 breaths/minute, which may be compared with a ground truth value of 15 breaths/minute measured for person 800 by a metronome.

FIG. 9 illustrates an example method 900 for determining the vital signs of a person. The vital signs may, for example, include the person's respiratory rate and heart rate.

Method 900 includes recording video images of a scene with an egocentric camera coupled to the person's body (910), detecting and magnifying image frame-to-image frame movements in the video images of the scene (920), and representing the magnified image frame-to-image frame movements in the video images of the scene by a one-dimensional (1D) amplitude-versus-time series (930). Method 900 further includes transforming the amplitude-versus-time series representation into a frequency spectrum (940), and identifying one or more local frequency maxima in the frequency spectrum as corresponding to one or more vital signs of the person (950).

In method 900, recording video images of a scene with the egocentric camera 910 may include capturing the image frames at a frame rate greater than 1500 frames/minute.

In method 900, magnifying image frame-to-image frame movements in the video images of the scene 920 may include video magnification under an Eulerian Video Magnification (EVM) framework and involves phase based pixel-by-pixel processing of the image frames.

In method 900, magnifying image frame-to-image frame movements 920 may include spatial decomposition of the image frames into layers to construct an image pyramid representation of the video images.

In method 900, magnifying image frame-to-image frame movements 920 may further include temporally processing each of the layers and magnifying each of the layers in at least one frequency range or band corresponding to a vital sign of the person.

In method 900, transforming the amplitude-versus-time series representation into a frequency spectrum 940 may include applying a sparsity test to select a sparse frequency spectrum for further processing and further include smoothing the selected sparse frequency spectrum by convolution with a kernel.

In method 900, identifying one or more local frequency maxima in the frequency spectrum as corresponding to one or more vital signs of the person 950 may include identifying one or more local frequency maxima in the smoothed frequency spectrum as corresponding to one or more vital signs of the person.

In method 900, the one or more vital signs of the person may, for example, include at least one of a respiration rate and a heart rate of the person.

Figure 10:
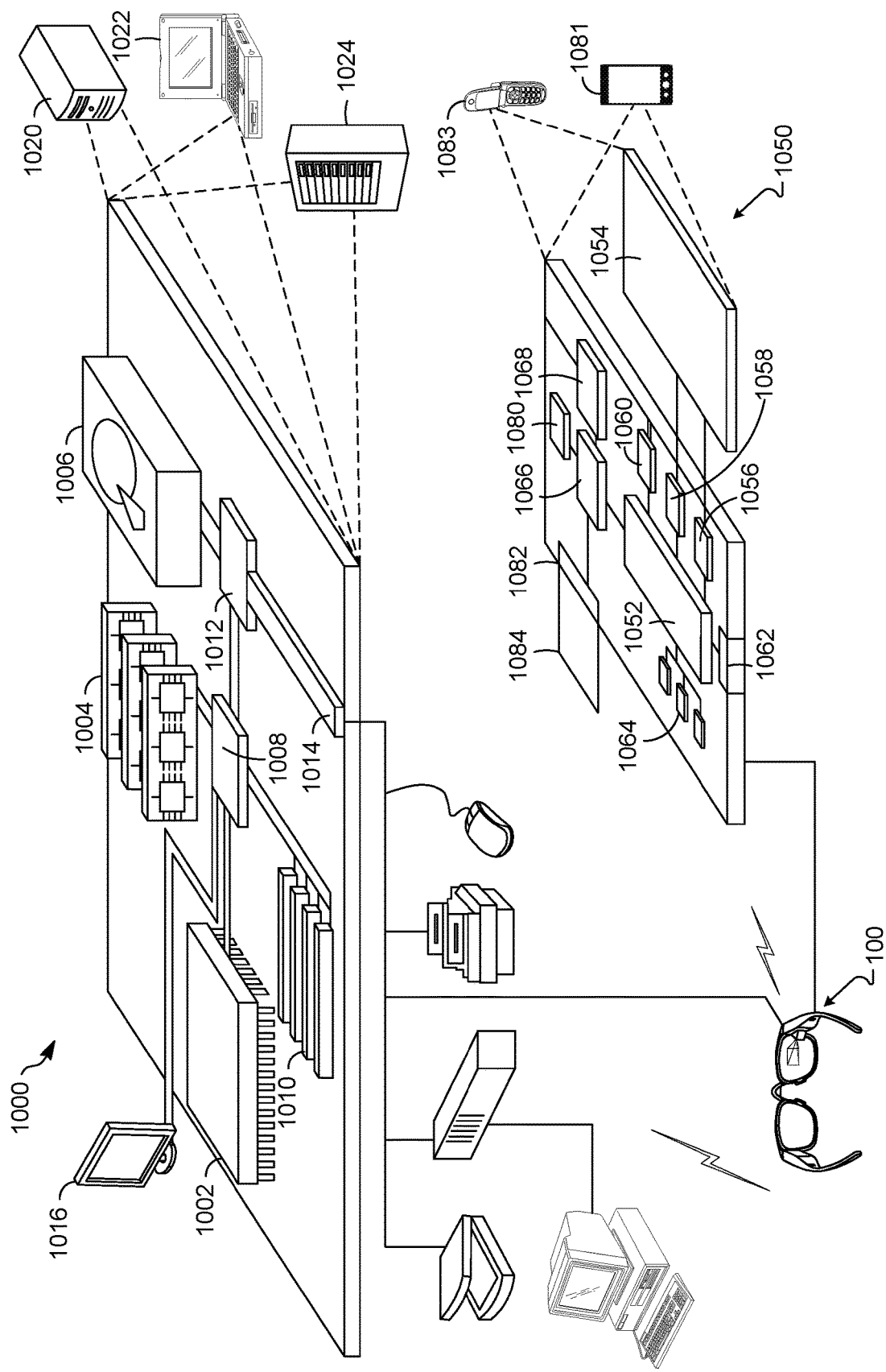
FIG. 10 is a block diagram illustrating an example of a computer device, a mobile computer device and a head mounted device, which may be used with the techniques described herein.

FIG. 10 shows an example of a computer device 1000 and a mobile computer device 1050, which may be used with the techniques described here. Computing device 1000 is intended to represent various forms of digital computers, such as laptops, desktops, tablets, workstations, personal digital assistants, smart devices, appliances, electronic sensor-based devices, televisions, servers, blade servers, mainframes, and other appropriate computing devices. Computing device 1050 is intended to represent various forms of mobile devices, such as personal digital assistants, cellular telephones, smart phones, and other similar computing devices. The components shown here, their connections and relationships, and their functions, are meant to be exemplary only, and are not meant to limit implementations described and/or claimed in this document.

Computing device 1000 includes a processor 1002, memory 1004, a storage device 1006, a high-speed interface 1008 connecting to memory 1004 and high-speed expansion ports 1010, and a low speed interface 1012 connecting to low speed bus 1010 and storage device 1006. The processor 1002 can be a semiconductor-based processor. The memory 1004 can be a semiconductor-based memory. Each of the components 1002, 1004, 1006, 1008, 1010, and 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as display 1016 coupled to high speed interface 1008. In other implementations, multiple processors and/or multiple buses may be used, as appropriate, along with multiple memories and types of memory. Also, multiple computing devices 1000 may be connected, with each device providing portions of the necessary operations (e.g., as a server bank, a group of blade servers, or a multi-processor system).

The memory 1004 stores information within the computing device 1000. In one implementation, the memory 1004 is a volatile memory unit or units. In another implementation, the memory 1004 is a non-volatile memory unit or units. The memory 1004 may also be another form of computer-readable medium, such as a magnetic or optical disk. In general, the computer-readable medium may be a non-transitory computer-readable medium.

The storage device 1006 is capable of providing mass storage for the computing device 1000. In one implementation, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods and/or computer-implemented methods, such as those described above. The information carrier is a computer- or machine-readable medium, such as the memory 1004, the storage device 1006, or memory on processor 1002.

The high speed controller 1008 manages bandwidth-intensive operations for the computing device 1000, while the low speed controller 1012 manages lower bandwidth-intensive operations. Such allocation of functions is exemplary only. In one implementation, the high-speed controller 1008 is coupled to memory 1004, display 1016 (e.g., through a graphics processor or accelerator), and to high-speed expansion ports 1010, which may accept various expansion cards (not shown). In the implementation, low-speed controller 1012 is coupled to storage device 1006 and low-speed expansion port 1010. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. It may also be implemented as part of a rack server system 1024. In addition, it may be implemented in a computer such as a laptop computer 1022. Alternatively, components from computing device 1000 may be combined with other components in a mobile device (not shown), such as device 1050. Each of such devices may contain one or more of computing device 1000, 1050, and an entire system may be made up of multiple computing devices 1000, 1050 communicating with each other.

Computing device 1050 includes a processor 1052, memory 1064, an input/output device such as a display 1054, a communication interface 1066, and a transceiver 1068, among other components. The device 1050 may also be provided with a storage device, such as a microdrive or other device, to provide additional storage. Each of the components 1050, 1052, 1064, 1054, 1066, and 1068, are interconnected using various buses, and several of the components may be mounted on a common motherboard or in other manners as appropriate.

The processor 1052 can execute instructions within the computing device 1050, including instructions stored in the memory 1064. The processor may be implemented as a chipset of chips that include separate and multiple analog and digital processors. The processor may provide, for example, for coordination of the other components of the device 1050, such as control of user interfaces, applications run by device 1050, and wireless communication by device 1050.

Processor 1052 may communicate with a user through control interface 1058 and display interface 1056 coupled to a display 1054. The display 1054 may be, for example, a TFT LCD (Thin-Film-Transistor Liquid Crystal Display) or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may be provided in communication with processor 1052, so as to enable near area communication of device 1050 with other devices. External interface 1062 may provide, for example, for wired communication in some implementations, or for wireless communication in other implementations, and multiple interfaces may also be used.

The memory 1064 stores information within the computing device 1050. The memory 1064 can be implemented as one or more of a computer-readable medium or media, a volatile memory unit or units, or a non-volatile memory unit or units. Expansion memory 1084 may also be provided and connected to device 1050 through expansion interface 1082, which may include, for example, a SIMM (Single In Line Memory Module) card interface. Such expansion memory 1084 may provide extra storage space for device 1050, or may also store applications or other information for device 1050. Specifically, expansion memory 1084 may include instructions to carry out or supplement the processes described above, and may include secure information also. Thus, for example, expansion memory 1084 may be provided as a security module for device 1050, and may be programmed with instructions that permit secure use of device 1050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1064, expansion memory 1084, or memory on processor 1052, that may be received, for example, over transceiver 1068 or external interface 1062.

Device 1050 may communicate wirelessly through communication interface 1066, which may include digital signal processing circuitry where necessary. Communication interface 1066 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1068. In addition, short-range communication may occur, such as using a Bluetooth, low power Bluetooth, Wi-Fi, or other such transceiver (not shown). In addition, GPS (Global Positioning System) receiver module 1080 may provide additional navigation- and location-related wireless data to device 1050, which may be used as appropriate by applications running on device 1050.

Device 1050 may also communicate audibly using audio codec 1060, which may receive spoken information from a user and convert it to usable digital information. Audio codec 1060 may likewise generate audible sound for a user, such as through a speaker, e.g., in a handset of device 1050. Such sound may include sound from voice telephone calls, may include recorded sound (e.g., voice messages, music files, etc.) and may also include sound generated by applications operating on device 1050.

The computing device 1050 may be implemented in a number of different forms, as shown in the figure. For example, it may be implemented as a cellular telephone 1083. It may also be implemented as part of a smart phone 1081, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as modules, programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor, or LED (light emitting diode)) for displaying information to the user and a keyboard and a pointing device (e.g., a mouse or a trackball) by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the computing devices depicted in FIG. 10 can include sensors that interface with, or are included in, a HMD1090. For example, one or more sensors included on computing device 1050 or other computing device depicted in FIG. 10, can provide input to HMD1090 or in general, provide input to that can be used by the HMD1090. The sensors can include, but are not limited to, a touchscreen, accelerometers, gyroscopes, pressure sensors, biometric sensors, temperature sensors, humidity sensors, and ambient light sensors. Computing device 1050 (e.g., the HMD1090) can use the sensors to determine an absolute position and/or a detected rotation of the HMD1090 that can then be used as input for use by the HMD1090.

In some implementations, one or more input devices included on, or connected to, the computing device 1050 and/or the HMD1090 can be used as inputs for use by the HMD1090. The input devices can include, but are not limited to, a touchscreen, a keyboard, one or more buttons, a trackpad, a touchpad, a pointing device, a mouse, a trackball, a joystick, a camera, a microphone, earphones or buds with input functionality, a gaming controller, or other connectable input device.

In some implementations, one or more output devices included on the computing device 1050, and/or in the HMD1090, can provide output and/or feedback to a user of the HMD1090. The output and feedback can be visual, tactical, or audio. The output and/or feedback can include, but is not limited to, rendering a display of the HMD1090, vibrations, turning on and off or blinking and/or flashing of one or more lights or strobes, sounding an alarm, playing a chime, playing a song, and playing of an audio file. The output devices can include, but are not limited to, vibration motors, vibration coils, piezoelectric devices, electrostatic devices, light emitting diodes (LEDs), strobes, and speakers.

In some implementations, computing device 1050 can be placed within HMD1090 to create an integrated HMD system. HMD1090 can include one or more positioning elements that allow for the placement of computing device 1050, such as smart phone 1081, in the appropriate position within HMD1090. In such implementations, the display of smart phone 1081 can render images using a display of the HMD1090.

In some implementations, the computing device 1050 may appear as another object in a computer-generated, 3D environment. Interactions by the user with the computing device 1050 (e.g., rotating, shaking, touching a touchscreen, swiping a finger across a touch screen) can be interpreted as interactions with the object in the AR/VR space. As just one example, computing device can be a laser pointer. In such an example, computing device 1050 appears as a virtual laser pointer in the computer-generated, 3D environment. As the user manipulates computing device 1050, the user in the AR/VR space sees movement of the laser pointer. The user receives feedback from interactions with the computing device 1050 in the AR/VR environment on the computing device 1050 or on the HMD1090.

In some implementations, a computing device 1050 may include a touchscreen. For example, a user can interact with the touchscreen in a particular manner that can mimic what happens on the touchscreen with what happens in a display of the HMD1090. For example, a user may use a pinching-type motion to zoom content displayed on the touchscreen. This pinching-type motion on the touchscreen can cause information provided in display to be zoomed. In another example, the computing device may be rendered as a virtual book in a computer-generated, 3D environment.

In some implementations, one or more input devices in addition to the computing device (e.g., a mouse, a keyboard) can be rendered in a display of the HMD1090. The rendered input devices (e.g., the rendered mouse, the rendered keyboard) can be used as rendered in the in the display.

A number of implementations have been described. Nevertheless, it will be understood that various modifications may be made without departing from the spirit and scope of the description and claims.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

Further to the descriptions above, a user is provided with controls allowing the user to make an election as to both if and when systems, programs, devices, networks, or features described herein may enable collection of user information (e.g., information about a user's social network, social actions, or activities, profession, a user's preferences, or a user's current location), and if the user is sent content or communications from a server. In addition, certain data may be treated in one or more ways before it is stored or used, so that user information is removed. For example, a user's identity may be treated so that no user information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

The computer system (e.g., computing device) may be configured to wirelessly communicate with a network server over a network via a communication link established with the network server using any known wireless communications technologies and protocols including radio frequency (RF), microwave frequency (MWF), and/or infrared frequency (IRF) wireless communications technologies and protocols adapted for communication over the network.

In accordance with aspects of the disclosure, implementations of various techniques described herein may be implemented in digital electronic circuitry, or in computer hardware, firmware, software, or in combinations of them. Implementations may be implemented as a computer program product (e.g., a computer program tangibly embodied in an information carrier, a machine-readable storage device, a computer-readable medium, a tangible computer-readable medium), for processing by, or to control the operation of, data processing apparatus (e.g., a programmable processor, a computer, or multiple computers). In some implementations, a tangible computer-readable storage medium may be configured to store instructions that when executed cause a processor to perform a process. A computer program, such as the computer program(s) described above, may be written in any form of programming language, including compiled or interpreted languages, and may be deployed in any form, including as a standalone program or as a module, component, subroutine, or other unit suitable for use in a computing environment. A computer program may be deployed to be processed on one computer or on multiple computers at one site or distributed across multiple sites and interconnected by a communication network.

Specific structural and functional details disclosed herein are merely representative for purposes of describing example implementations. Example implementations, however, may be embodied in many alternate forms and should not be construed as limited to only the implementations set forth herein.

The terminology used herein is for the purpose of describing particular implementations only and is not intended to be limiting of the implementations. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of the stated features, steps, operations, elements, and/or components, but do not preclude the presence or addition of one or more other features, steps, operations, elements, components, and/or groups thereof.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present. As used herein the term "and/or" includes any and all combinations of one or more of the associated listed items.

Spatially relative terms, such as "beneath," "below," "lower," "above," "upper," and the like, may be used herein for ease of description to describe one element or feature in relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 130 degrees or at other orientations) and the spatially relative descriptors used herein may be interpreted accordingly.

Example implementations of the concepts are described herein with reference to cross-sectional illustrations that are schematic illustrations of idealized implementations (and intermediate structures) of example implementations. As such, variations from the shapes of the illustrations as a result, for example, of manufacturing techniques and/or tolerances, are to be expected. Thus, example implementations of the described concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example implementations.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present implementations.

Unless otherwise defined, the terms (including technical and scientific terms) used herein have the same meaning as commonly understood by one of ordinary skill in the art to which these concepts belong. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

While certain features of the described implementations have been illustrated as described herein, many modifications, substitutions, changes, and equivalents will now occur to those skilled in the art. It is, therefore, to be understood that the appended claims are intended to cover such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components, and/or features of the different implementations described.

What is claimed is:

1. A computer program product, the computer program product being tangibly embodied on a non-transitory computer-readable storage medium and comprising instructions that, when executed by at least one computing device coupled to an egocentric camera disposed on a person, are configured to cause the at least one computing device to:
   record video images of a scene using the egocentric camera;
   detect and magnify image frame-to-image frame movements in the video images of the scene;
   represent the magnified image frame-to-image frame movements in the video images of the scene by a one-dimensional (1D) amplitude-versus-time series;
   transform the 1D amplitude-versus-time series representation into a frequency spectrum; and
   identify one or more local frequency maxima in the frequency spectrum as corresponding to one or more vital signs of the person.

2. The computer program product of claim 1, wherein the instructions, when executed, are further configured to cause the at least one computing device to:
   record video images of the scene at a frame rate greater than approximately 1500 frames/minute.

3. The computer program product of claim 1, wherein the instructions, when executed, are further configured to cause the at least one computing device to:
   magnify image frame-to-image frame movements in the video images of the scene under an Eulerian Video Magnification (EVM) framework that involves phase based pixel-by-pixel processing of the image frames.

4. The computer program product of claim 1, wherein the instructions, when executed, are further configured to cause the at least one computing device to:

spatially decompose the image frames into layers to construct an image pyramid representation of the video images.

5. The computer program product of claim 4, wherein the instructions, when executed, are further configured to cause the at least one computing device to:
temporally process each of the layers and magnify each of the layers in at least one frequency band corresponding to a vital sign of the person.

6. The computer program product of claim 1, wherein the instructions, when executed, are further configured to cause the at least one computing device to:
apply a sparsity test to the frequency spectrum and select a sparse frequency spectrum for further processing.

7. The computer program product of claim 6, wherein the instructions, when executed, are further configured to cause the at least one computing device to:
smooth the selected sparse frequency spectrum by convolution with a kernel.

8. The computer program product of claim 7, wherein the instructions, when executed, are further configured to cause the at least one computing device to:
identify one or more local frequency maxima in the smoothed frequency spectrum as corresponding to one or more vital signs of the person.

9. The computer program product of claim 8, wherein the one or more vital signs of the person include at least one of a respiration rate and a heart rate of the person.

10. A method comprising:
recording video images of a scene with an egocentric camera coupled to a person's body;
detecting and magnifying image frame-to-image frame movements in the video images of the scene;
representing the magnified image frame-to-image frame movements in the video images of the scene by a one-dimensional (1D) amplitude-versus-time series;
transforming the 1D amplitude-versus-time series representation into a frequency spectrum; and
identifying one or more local frequency maxima in the frequency spectrum as corresponding to one or more vital signs of the person.

11. The method of claim 10, wherein recording video images of a scene with the egocentric camera includes capturing the image frames at a frame rate greater than approximately 1500 frames/minute.

12. The method of claim 10, wherein magnifying image frame-to-image frame movements in the video images of the scene includes video magnification under an Eulerian Video Magnification (EVM) framework and involves phase based pixel-by-pixel processing of the image frames.

13. The method of claim 12, wherein magnifying image frame-to-image frame movements includes spatially decomposing the image frames into layers to construct an image pyramid representation of the video images.

14. The method of claim 13, wherein magnifying image frame-to-image frame movements further includes temporally processing each of the layers and magnifying each of the layers in at least one frequency band corresponding to a vital sign of the person.

15. The method of claim 10, wherein transforming the 1D amplitude-versus-time series representation into a frequency spectrum further includes applying a sparsity test to select a sparse frequency spectrum for further processing.

16. The method of claim 15, wherein transforming the 1D amplitude-versus-time series representation into a frequency spectrum further includes smoothing the selected sparse frequency spectrum by convolution with a kernel.

17. The method of claim 16, wherein identifying one or more local frequency maxima in the frequency spectrum as corresponding to one or more vital signs of the person includes identifying one or more local frequency maxima in the smoothed frequency spectrum as corresponding to one or more vital signs of the person.

18. The method of claim 10, wherein the one or more vital signs of the person include at least one of a respiration rate and a heart rate of the person.

19. A computing device comprising:
a processor; and
a storage medium storing instructions;
wherein the instructions, when executed by the processor, cause the computing device to:
record video images of a scene using an egocentric camera coupled to a person's body;
detect and magnify image frame-to-image frame movements in the video images of the scene;
represent the magnified image frame-to-image frame movements in the video images of the scene by a one-dimensional (1D) amplitude-versus-time series;
transform the 1D amplitude-versus-time series representation into a frequency spectrum; and
identify one or more local frequency maxima in the frequency spectrum as corresponding to one or more vital signs of the person.

20. The computing device of claim 19, wherein the computing device includes at least one or more of a smartwatch, smartglasses, a smartphone, a server, or a remote computer.

* * * * *